United States Patent [19]

Cross et al.

[11] Patent Number: 5,281,601
[45] Date of Patent: Jan. 25, 1994

[54] MUSCARINIC RECEPTOR ANTAGONISTS

[75] Inventors: Peter E. Cross, Canterbury; Alexander R. Mackenzie, Deal, both of England

[73] Assignee: Pfizer Inc., New York, N.Y.

[21] Appl. No.: 859,489

[22] PCT Filed: Nov. 28, 1989

[86] PCT No.: PCT/EP90/02042

§ 371 Date: Jun. 12, 1992

§ 102(e) Date: Jun. 12, 1992

[87] PCT Pub. No.: WO91/09015

PCT Pub. Date: Jun. 27, 1991

[30] Foreign Application Priority Data

Dec. 12, 1989 [GB] United Kingdom ............... 8928941

[51] Int. Cl.$^5$ ............... A61K 31/445; C07D 405/14; C07D 401/04; C07D 401/14
[52] U.S. Cl. ............... 514/320; 514/255; 514/318; 514/326; 546/193; 546/196; 546/208; 544/336; 544/408; 544/410
[58] Field of Search ............... 546/208, 196, 193; 544/408, 410, 336; 514/255, 318, 320, 326

[56] References Cited

U.S. PATENT DOCUMENTS 5,037,841 8/1991 Schohe ............... 546/157

FOREIGN PATENT DOCUMENTS 1024521 5/1972 United Kingdom .

*Primary Examiner*—C. Warren Ivy
*Assistant Examiner*—Celia Chang
*Attorney, Agent, or Firm*—Peter C. Richardson; Paul H. Ginsburg

[57] ABSTRACT

A series of novel 3-phenyl-3-[1-(cyclicalkyl)pyrrolidin-3-yl]glutarimide derivatives have been prepared, including their pharmaceutically acceptable salts. The cyclic moiety present in these compounds is derived from either benzene or a heteroaryl such as benzofuran or 2,3-dihydrobenzofuran, or it is derived from an aromatic heterocyclic such as pyridine, pyrazine or thiophene, and it is attached to the adjacent alkyl group of the molecule by means of one of the available ring carbon atoms situated in the aromatic ring of the aforementioned cyclic ring moiety. These particular compounds are useful in therapy as selective muscarinic receptor antagonists, which are selective for smooth muscle muscarinic sites over cardiac muscarinic sites and therefore, are of value in the treatment of diseases associated with altered motility and/or smooth muscle tone as found in the gut, trachea and bladder. Methods for preparing these compounds from known starting materials are provided.

10 Claims, No Drawings

MUSCARINIC RECEPTOR ANTAGONISTS

BACKGROUND OF THE INVENTION

This invention relates to certain 3-substituted pyrrolidine derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

SUMMARY OF THE INVENTION

According to the invention there are provided compounds of the formula:

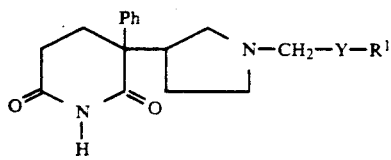

and their pharmaceutically acceptable salts, wherein
Y is a direct link, $-CH_2-$, $-(CH_2)_2-$, $-CH_2O-$ or $-CH_2S-$; and
$R^1$ is a group of the formula:

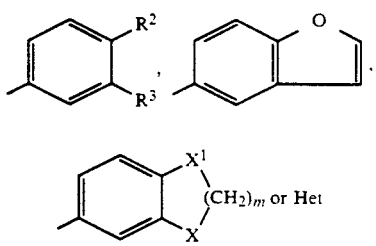

where
$R^2$ and $R^3$ are each independently H, $C_1$-$C_4$ alkyl, $C_1$-$C_4$ alkoxy, $-(CH_2)_nOH$, halo, trifluoromethyl, cyano, $-(CH_2)_nNR^4R^5$, $-CO(C_1$-$C_4$ alkyl), $-O$-$CO(C_1$-$C_4$ alkyl), $-CH(OH)(C_1$-$C_4$ alkyl), $-C$-$(OH)(C_1$-$C_4$ alkyl)$_2$, $-SO_2NH_2$, $-(CH_2)_nCONR^4R^5$ or $-(CH_2)_nCOO(C_1$-$C_4$ alkyl);
$R^4$ and $R^5$ are each independently H or $C_1$-$C_4$ alkyl;
n is 0, 1 or 2;
X and $X^1$ are each independently O or $CH_2$;
m is 1, 2 or 3; and
"Het" is pyridyl, pyrazinyl or thienyl.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

m is preferably 1.

$R^1$ is preferably a group of the formula:

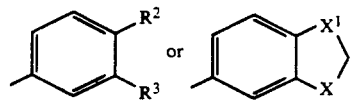

where $R^2$ and $R^3$ are each independently selected from H, halo and hydroxy, and X and $X^1$ are as defined above.

$R^1$ is most preferably:

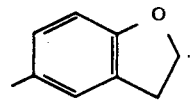

Y is preferably a direct link, $-CH_2-$ or $-(CH_2)_2-$.
Y is most preferably $-CH_2-$.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1-19. These salts can be prepared conventionally, e.g. by mixing a solution of the free base and the acid in a suitable solvent, e.g. ethanol, and recovering the acid addition salt either as a precipitate, or by evaporation of the solution.

DETAILED DESCRIPTION OF THE INVENTION

The compounds of the formula (I) can be prepared by a number of routes, including the following:

Route A

This can be illustrated as follows:

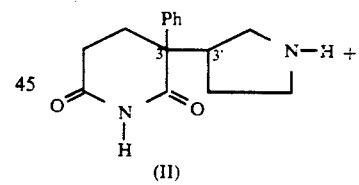

(II)

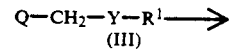

Compounds (I)

Y and $R^1$ are as defined for formula (I) and Q is a leaving group, e.g. Br, Cl, I, $C_1$-$C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium bicarbonate, sodium or potassium carbonate, triethylamine or pyridine, and in a suitable organic solvent, e.g. dimethylformamide or acetonitrile, at up to the reflux temperature. Reaction temperatures of 60°-120° are generally desirable and it is most convenient to carry out the reaction under reflux. Compound (II) can be used in acid-addition salt form (e.g. as a hydrobromide or formate) provided an excess of base is present. Iodo is often a particularly suitable leaving group but since the starting materials (III) are sometimes most conveniently available as chlorides the reaction can also be carried out using the compound (III) as a chloride but in the presence of an iodide such as sodium or potassium iodide. The product (I) can be isolated and purified conventionally.

Starting materials having appropriate stereochemistry at the 3- and 3'-positions should be used so as to obtain end products having the desired stereo chemistry.

The starting materials of the formula (II) can be obtained by conventional procedures such as those described in the following Preparations section. The starting materials in the formula (III) are in general known compounds which can be prepared by conventional techniques. The preparation of any novel starting materials of the formula (III) used in the Examples is however described in the following Preparations section.

Route B

This involves the cyclisation of an intermediate of the formula (IV) by heating it with concentrated mineral acid, preferably concentrated hydrochloric acid and under reflux:

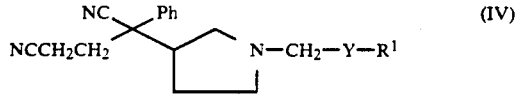
(IV)

The starting materials (IV) are obtainable conventionally and as is indicated in the following Preparations section.

Route C

This route is useful for preparing compounds in which Y is —CH$_2$— and R$^1$ is 2- or 4-pyridyl or pyrazinyl and involves reacting a compound of the formula (II)—see Route A—with 2- or 4-vinylpyridine or 2-vinylpyrazine.

The reaction is typically carried out with heating, e.g. at about 60° to 110° C. and preferably under reflux, in a suitable organic solvent, e.g. dioxan. In some instances, the use of a basic (preferably a strong base which is soluble in an organic solvent such as N-benzyltrimethylammonium hydroxide ["Triton B"]) or acidic (preferably a C$_1$-C$_4$ alkanoic acid) catalyst may be beneficial.

Some of the compounds of the formula (I) in which R$^1$ is a substituted phenyl group can be converted to other compounds of the formula (I) as follows:

(a) A —CO$_2$(C$_1$-C$_4$ alkyl) substituent on the phenyl group can be selectively reduced to —CH$_2$OH. Lithium aluminium hydride is the most suitable reducing agent. The reaction is typically carried in a suitable organic solvent, e.g. ether, at between 0° and room temperature. It is generally most convenient to use the starting material in the form of its methyl ester.

(b) A hydroxy substituent on the phenyl group can be converted to —OCO(C$_1$-C$_4$ alkyl) by acylation using a C$_1$-C$_4$ alkanoyl chloride or bromide, or an alkanoic anhydride of the formula (C$_1$-C$_4$ alkyl.CO)$_2$O. The presence of an acid acceptor is preferable. The reaction is typically carried out at about room temperature in a suitable organic solvent, e.g. dioxan.

(c) A —CO(C$_1$-C$_4$ alkyl) substituent on the phenyl group can be reduced to a substituent of the formula —CH(OH) (C$_1$-C$_4$ alkyl). A suitable reducing agent is sodium borohydride. The reaction is typically carried out at between 0° and room temperature in a suitable organic solvent, e.g. methanol.

(d) A —(CH$_2$)$_n$COO(C$_1$-C$_4$ alkyl) substituent, preferably where the alkyl group is methyl, can be converted to —(CH$_2$)$_n$CONR$^4$R$^5$ by reaction with ammonia or the appropriate amine R$^4$R$^5$NH. When R$^4$ and R$^5$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may poceed at a satisfactory rate at room temperature, heating at up to 120°, preferably 60° to 100° C., is generally necessary. For volatile amines, the reaction is best carried out in a bomb.

(e) A hydroxy substituent can be converted to C$_1$-C$_4$ alkoxy firstly by reaction with a base such as potassium carbonate, and secondly by reaction with a C$_1$-C$_4$ alkyl iodide or bromide. The reaction is typically carried out in a solvent such as dioxan or acetone, and preferably under reflux. (f) A hydroxymethyl or hydroxyethyl substituent on the phenyl group can be converted to —CH$_2$NR$^4$R$^5$ or —(CH$_2$)$_2$NR$^4$R$^5$ firstly by reaction with thionyl chloride and secondly by reaction with ammonia or the appropriate amine R$^4$R$^5$NH. The reaction with thionyl chloride is typically carried out with heating, preferably under reflux, in a solvent such as methylene chloride. The reaction with ammonia or the amine is typically carried out with heating, preferably under reflux, in a solvent such as methylene chloride. The reaction with ammonia or the amine is typically carried out at in a solvent such as ethanol, and heating, e.g. under reflux, may be necessary.

(g) A —CO(C$_1$-C$_4$ alkyl) substituent can be converted to —C(OH) (C$_1$-C$_4$ alkyl)$_2$ by reaction with a C$_1$-C$_4$ alkyllithium or C$_1$-C$_4$ alkylmagnesium bromide, chloride, or iodide (e.g. methyllithium, methylmagnesium bromide, methylmagnesium iodide or methylmagnesium chloride). The reaction is typically carried out in a solvent such as ether at a temperature of from 0° C. to room temperature, and (h) An iodo substituent can be converted to C$_1$-C$_4$ alkoxycarbonyl by reaction, typically at about room temperature, with carbon monoxide in a C$_1$-C$_4$ alkanol containing a base [e.g. potassium carbonate] and a palladium (II) catalyst [e.g. bis(triphenylphosphine)palladium (II) chloride].

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% O$_2$ and 5% CO$_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined (pA$_2$ value—Arunlakshana and Schild (1959), Brit. J. Pharmacol., 14, 48-58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to main in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being with an effective amount of a compound of the formula (I), or a pharmaceutically acceptable salt or composition thereof.

The invention also includes the novel intermediates of the formula (II).

In the following Examples and Preparations, where the stereochemistry at the 3-position of the glutarimide ring was not R,S, no determination of whether the compound was in the 3R or 3S form was carried out. Thus such compounds are simply referred to as "3-(R or S)", or "3-(S or R)- where the isomer is clearly the opposite of the previous one.

The Examples illustrate the preparation of the compounds of the formula (I), and the Preparations illustrate the preparation of certain of the starting materials used in the preceding Examples.

EXAMPLE 1

(A) Preparation of 3-(R or S)-3'-(S)-3-phenyl-3-[1-{2-(4-fluorophenyl)ethyl}pyrrolidin-3-yl]glutarimide

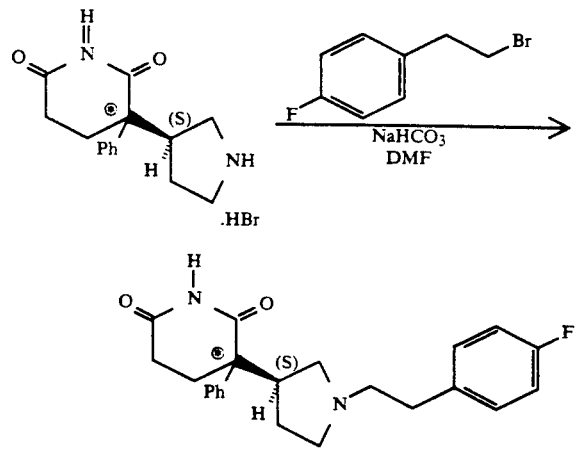

Ⓡ (R) or (S)

A mixture containing 3-(R or S)-3'-(S)-3-phenyl-3-(pyrrolidin-3-yl)glutarimide hydrobromide (0.4 g—see Preparation 11), 4-fluorophenethyl bromide (0.17 g), sodium bicarbonate (0.4 g) and dimethylformamide (8 ml) was heated at 100° C. for 30 minutes. On cooling to room temperature the mixture was concentrated in vacuo and the residue was partitioned between dichloromethane (50 ml) and water (50 ml). The layers were separated and the aqueous layer was further extracted with dichloromethane (3×50 ml). The combined dichloromethane extracts were dried (MgSO4) and concentrated in vacuo to give a foam which was purified by column chromatography on silica eluting with dichloromethane containing methanol (4%). The product-containing fractions were combined and concentrated in vacuo to give the title compound as a foam, yield 0.03 g, $[\alpha]_D^{25}$ +148° (c 0.55, DMF).

Analysis %: Found: C,70.88; H,6.92; N,6.32. Calculated for $C_{23}H_{25}FN_2O_2.\frac{3}{4}$ MeOH: C,70.52; H,6.98; N,6.92.

$^1$H-N.M.R. (d$^6$DMSO) δ=7.50-7.25 (m, 5H); 7.25-7.15 (m, 2H); 7.15-6.95 (m, 2H); 2.80-2.00 (m, 13H); 1.80-1.60 (m, 2H) ppm.

(B) A similar procedure starting with 3-(S or R)-3'-(S)-phenyl-3-(pyrrolidin-3-yl)glutarimide hydrobromide (0.8 g—see Preparation 12) gave 3-(S or R)-3'-(S)-3-[1-{2-(4-fluorophenyl)ethyl}pyrrolidin-3-]glutarimide, yield 0.05 g, m.p. 152° C.

Analysis: Found: C,72.49; H,6.88; N,7.49. Calculated for $C_{23}H_{25}FN_2O_2$: C,72.60; H,6.62; N,7.36.

$^1$H-N.M.R. (CDCl$_3$) δ=7.95-7.85 (brs, 1H); 7.50-7.25 (m, 5H); 7.20-7.10 (m, 2H); 7.05-6.90 (m, 2H); 3.10-2.95 (m, 1H); 2.80-2.25 (m, 12H); 1.75-1.55 (m, 2H) ppm.

(C) A similar procedure starting with 3-(R or S)-3'-(R)-phenyl-3-(pyrrolidin-3-yl)glutarimide hydrobromide (0.4 g—see Preparation 10) gave 3-(R or S)-3'-(R)-3-[1-{2-(4-fluorophenyl)ethyl}pyrrolidin-3-yl]glutarimide, yield 0.09 g, $[\alpha]_D^{25}$ −129° (c 0.5, DMF).

Analysis %: Found: C,68.56; H,6.42; N,6.71. Calculated for $C_{23}H_{25}FN_2O_2.H_2O.1/20\ CH_2Cl_2$: C,68.74; H,6.77; N,6.96.

$^1$H-N.M.R. (CDCl$_3$) δ=8.10-7.85 (brs, 1H); 7.50-7.25 (m, 5H); 7.20-7.10 (m, 2H); 7.10-6.90 (m, 2H); 3.10-2.90 (m, 1H); 2.90-2.15 (m, 12H); 2.05-1.70 (m, 2H) ppm.

(D) A similar procedure starting with 3-(S or R)-3'-(R)-phenyl-3-(pyrrolidin-3-yl)glutarimide hydrobromide (0.4 g—see Preparation 9) gave 3-(S or R)-3'-(R)-3-[1-{2-(4-fluorophenyl)ethyl}pyrrolidin-3-yl]glutarimide, yield 0.11 g, $[\alpha]_D^{25}$ +152° (c 0.5, DMF).

Analysis %: Found: C,70.20; H,6.49; N,7.05. Calculated for $C_{23}H_{25}FN_2O_2.1/5\ CH_2Cl_2$: C,70.10; H,6.39; N,7.05.

$^1$H-N.M.R. (CDCl$_3$)δ=8.20-8.00 (brs, 1H); 7.60-7.25 (m, 5H); 7.20-7.10 (m, 2H); 7.00-6.90 (m, 2H); 3.10-2.95 (m, 1H); 2.85-2.25 (m, 12H); 1.85-1.60 (m, 2H) ppm.

EXAMPLE 2

Preparation of 3-(R or S)-3'-(S)-3-phenyl-3-[1-{3-(4-hydroxyphenyl)propyl}pyrrolidin-3-yl]glutarimide

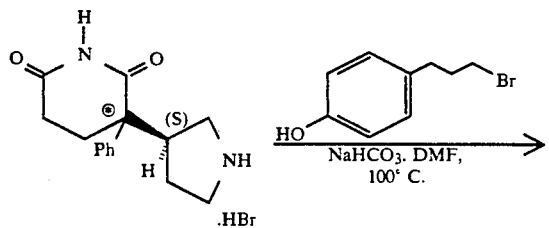

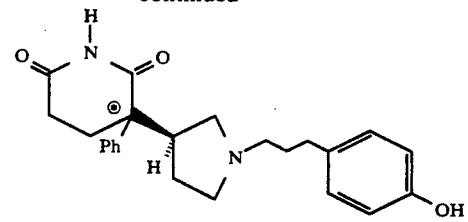

Ⓢ (R) or (S)

A mixture containing 3-(R or S)-3'-(S)-3-phenyl-3-(pyrrolidin-3-yl)glutarimide hydrobromide (0.3 g—see Preparation 11), 1-bromo-3-(4-hydroxyphenyl)propane (0.15 g—see Acta Pharm. Suec., 1974, 11, 33), sodium bicarbonate (0.5 g) and dimethylformamide (3 ml) was heated at 100° C. for 20 minutes then allowed to cool to room temperature. Water (20 ml) was added and the mixture was extracted with dichloromethane (3×15 ml). The combined dichloromethane extracts were dried (MgSo4) and concentrated in vacuo to give an oil which was purified by trituration with diisopropyl ether to give the title compound as a colourless microcrystalline solid, yield 0.05 g, m.p. 89° C.

Analysis %: Found: C,70.36; H,7.48; N,6.28. Calculated for $C_{24}H_{28}N_2O_3.H_2O$: C,7.22; H,7.37; N,6.82.

$^1$H-N.M.R. (d$^6$DMSO) δ=9.10 (s, 1H); 7.50-7.25 (m, 5H); 6.95-6.90 (d, 2H); 6.70-6.60 (d, 2H); 2.85-2.70 (m, 1H); 2.55-2.30 (m, 4H); 2.35-2.05 (m, 8H); 1.75-1.50 (m, 4H) ppm.

EXAMPLE 3

Preparation of 3-(R or S)-3'-(S)-3-phenyl-3-[1-{2-(4-chlorophenyl)ethyl}pyrrolidin-3-yl]glutarimide

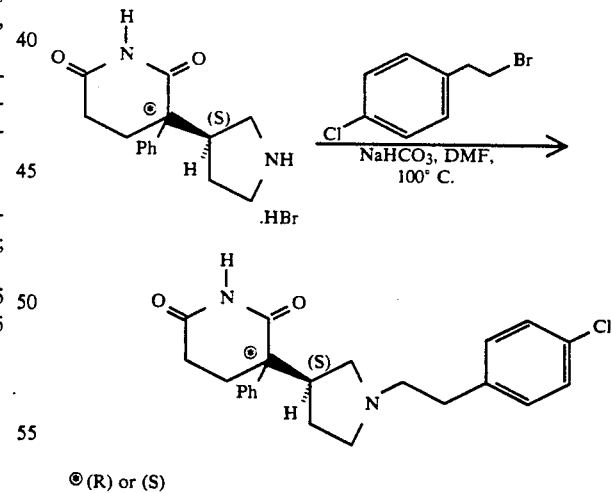

Ⓢ (R) or (S)

A mixture containing 3-(R or S)-3'-(S)-3-phenyl-3-(pyrrolidin-3-yl)glutarimide hydrobromide (0.4 g—see Preparation 11), 4-chlorophenethyl bromide (0.21 g), sodium bicarbonate (1 g) and dimethylformamide (4 ml) was heated at 100° C. for 30 minutes then allowed to cool to room temperature. Water (30 ml) was added and the mixture was extracted with diethyl ether (3×30 ml). The combined ethereal extracts were dried (MgSO4) and concentrated in vacuo to give a foam which was purified by trituration with diethyl ether (40 ml) to give the title compound as a colourless microcrystalline solid, yield 0.105 g, m.p. 205°–208° C.

Analysis %: Found: C, 69.34; H,6.54; N,7.01. Calculated for $C_{23}H_{25}ClN_2O_2$: C,69.59; H,6.35; N,7.06.

$^1$H-N.M.R. (d$^6$DMSO) δ=7.45–7.25 (m, 7H); 7.25–7.15 (d, 2H); 2.80–2.70 (m, 1H); 2.70–2.30 (m, 9H); 2.25–2.10 (m, 3H); 1.75–1.60 (m, 2H) ppm.

EXAMPLE 4

Preparation of 3-(R or S)-3'-(S)-3-phenyl-3-[1-{3-(4-fluorophenyl)propyl}pyrrolidin-3-yl]glutarimide

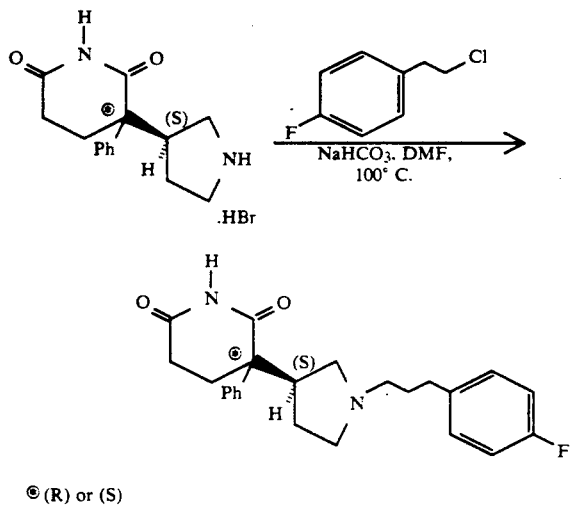

A mixture containing 3-(R or S)-3'-(S)-3-phenyl-3-(pyrrolidin-3-yl)glutarimide hydrobromide (0.4 g—see Preparation 11), 1-chloro-3-(4-fluorophenyl)propane (0.18 g—see USP 4051190), sodium bicarbonate (1.2 g) and dimethylformamide (3 ml) was heated at 100° C. for 20 minutes then allowed to cool to room temperature. Water (20 ml) was added and the mixture was extracted with diethyl ether (3×30 ml). The combined ethereal extracts were dried (MgSO$_4$) and concentrated in vacuo to give a foam which was purified by trituration with diethyl ether to give the title compound as a colourless microcrystalline solid, yield 0.074 g, m.p. 197° C.

Analysis %: Found: C,72.33; H,7.12; N,6.98. Calculated for $C_{24}H_{27}FN_2O_2.\frac{1}{4} H_2O$: C,72.24; H,6.88; N,7.02.

$^1$H-N.M.R. (d$^6$DMSO) δ=7.45–7.25 (m, 5H); 7.20–7.10 (m, 2H); 7.10–7.00 (m, 2H); 2.85–2.70 (m, 1H); 2.60–2.35 (m, 7H); 2.35–2.05 (m, 6H); 1.75–1.50 (m, 3H) ppm.

EXAMPLE 5

Preparation of 3-(R or S)-3'-(S)-3-phenyl-3-{1-(3-phenylpropyl)-pyrrolidin-3-yl}glutarimide

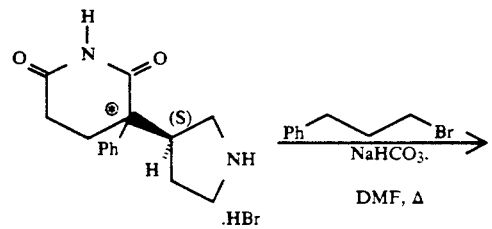

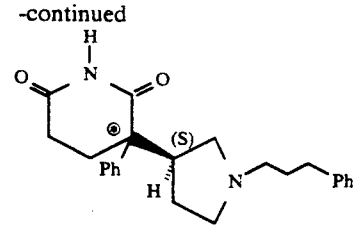

A mixture containing 3-(R or S)-3'-(S)-3-phenyl-3-(pyrrolidin-3-yl)glutarimide hydrobromide (0.5 g—see Preparation 11), sodium bicarbonate (0.5 g), 1-phenyl-3-bromopropane (0.232 g) and dimethylformamide (5 ml) was heated at 100° C. for 20 minutes. On cooling to room temperature water (50 ml) was added and the mixture extracted with diethyl ether (3×30 ml). The combined ethereal extracts were dried (Na$_2$SO$_4$) and concentrated in vacuo to give a solid which was purified by trituration with diethyl ether to give the title compound as a colourless microcrystalline solid, yield 0.12 g, m.p. 189° C.

Analysis % Found: C,76.21; H,7.61; N,7.61, Calculated for $C_{24}H_{28}N_2O_2$: C,76.56; H,7.49; N,7.44.

$^1$H-N.M.R.: (d$^6$DMSO) δ=7.45–7.10 (m,10H); 2.85–2.70 (m, 1H); 2.60–2.35 (m, 7H); 2.40–2.05 (m, 6H); 1.75–1.55 (m, 3H) ppm.

EXAMPLE 6

Preparation of 3-(R or S)-3'-(S)-3-phenyl-3-[1-{2-(2,3-dihydrobenzofuran-5-yl)ethyl}pyrrolidin-3-yl]glutarimide

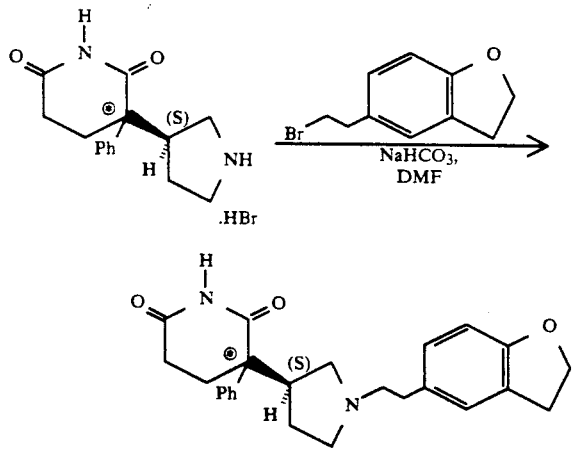

A mixture containing 3-(R or S)-3'-(S)-3-phenyl-3-(pyrrolidin-3-yl)glutarimide hydrobromide (0.5 g—see Preparation 11), 5-(2-bromoethyl)-2,3-dihydrobenzofuran (0.25 g—see Preparation 17), sodium bicarbonate (0.5 g) and dimethylformamide (3 ml) was heated at 100° C. for 20 minutes then allowed to cool to room temperature. Water (30 ml) was added and the mixture was extracted with diethyl ether (3×30 ml). The combined ethereal extracts were dried (MgSO$_4$) and concentrated in vacuo to give a foam which was purified by trituration with diethyl ether (20 ml) to give the title compound as a colourless microcrystalline solid, yield 0.043 g, m.p. 193° C.

Analysis %: Found: C,70.81; H,6.78; N,6.29. Calculated for $C_{25}H_{28}N_2O_3.H_2O$: C,71.06; H,7.16; N,6.63.

$^1$H-N.M.R. (d$^6$DMSO) δ=7.45-7.25 (m, 5H); 7.05 (s, 1H); 6.90-6.85 (d, 1H); 6.65-6.60 (d, 1H); 4.50-4.40 (m, 2H); 3.15-3.05 (m, 2H); 2.85-2.70 (m, 1H); 2.65-2.30 (m, 9H); 2.30-2.10 (m, 3H); 1.75-1.60 (m, 2H) ppm.

EXAMPLE 7

Preparation of 3-(R,S)-3'-(R,S)-3-phenyl-3-(N-benzylpyrrolidin-3-yl)glutarimide

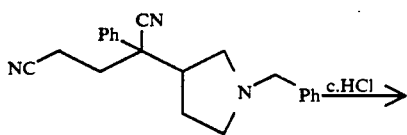

A solution of 3-(R,S)-1'-(R,S)-3-(1,3-dicyano-1-phenylprop-1-yl)-N-benzylpyrrolidine (2.9 g—see Preparation 14) in concentrated hydrochloric acid (10 ml) was heated under reflux for 2 hours. On cooling to room temperature the mixture was basified (pH 11) by the addition of aqueous potassium carbonate solution then extracted with dichloromethane (2×30 ml). The combined dichloromethane extracts were dried (MgSO$_4$) and concentrated in vacuo to give the title compound as a colourless foam, yield 2.9 g.

Analysis %: Found: C,73.71; H,6.86; N,7.56. Calculated for $C_{22}H_{24}N_2O_2.1/16$ $CH_2Cl_2$: C,73.43; H,6.76; N,7.72.

$^1$H-N.M.R. (CDCl$_3$) δ=8.00-7.85 (brs), 7.45-7.20 (m), 3.70-3.50 (m), 3.10-2.90 (m), 2.70-2.20 (m), 1.95-1.85 (m), 1.85-1.70 (m), 1.70-1.60 (m) ppm.

EXAMPLE 8

Preparation of 3-(R,S)-3'-(R,S)-3-phenyl-3-{1-(2-phenylethyl)pyrrolidin-3-yl}glutarimide

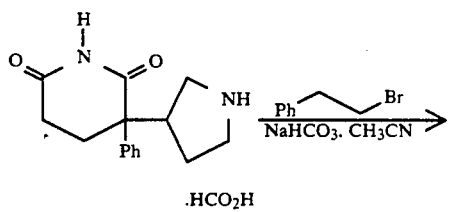

A mixture containing 3-(R,S)-3'-(R,S)-3-phenyl-3-(pyrrolidin-3-yl)glutarimide formate (1.75 g—see Preparation 15), phenethyl bromide (1.4 g), sodium bicarbonate (4 g) and acetonitrile (20 ml) was heated under reflux for 5 hours. The mixture was filtered and the filtrate was concentrated in vacuo to give a gum which was purified by column chromatography on silica eluting with dichloromethane containing methanol (25%). The product-containing fractions were combined and concentrated in vacuo to give the title compound as a gum, yield 0.6 g.

Analysis %: Found: C,75.22; H,7.04; N,7.67. Calculated for $C_{23}H_{26}N_2O_2.1/10$ $CH_2Cl_2$: C,74.44; H, 7.09; N,7.51.

$^1$H-N.M.R. (CDCl$_3$) δ=8.05-7.90 (brs), 7.45-7.10 (m), 3.10-2.90 (m), 2.85-2.20 (m), 2.00-1.85 (m), 1.80-1.55 (m) ppm.

PREPARATION 1

Preparation of 3-(R)-(−)-hydroxypyrrolidine hydrochloride

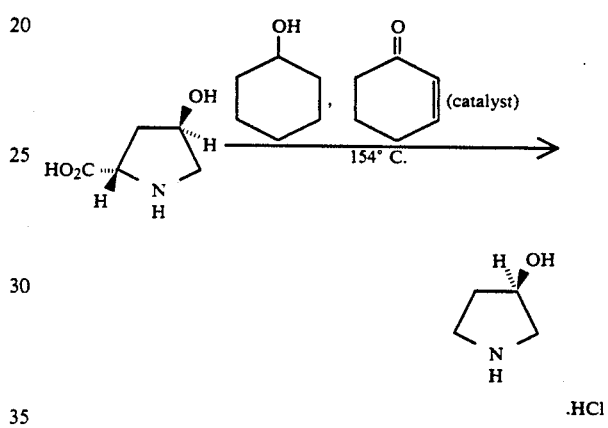

(2S,4R)-(−)-4-Hydroxy-2-pyrrolidinecarboxylic acid (40 g—commercially available), anhydrous cyclohexanol (200 ml) and 2-cyclohexen-1-one (2 ml) were heated together at 154° C. for 4.5 hours at which point the mixture was homogenous. On cooling to room temperature, saturated ethanolic hydrogen chloride (150 ml) was added and the resulting crystalline solid was filtered off and washed with ethyl acetate (2×50 ml). The solid was recrystallised from isopropanol to give the title compound as colourless crystals, yield 19.15 g, m.p. 104°-108° C., [α]$_D^{25}$−8.0° (c 3.45, CH$_3$OH).

$^1$H-N.M.R. (d$^6$DMSO), δ=10.00-8.60 (brs, 2H); 5.55-5.20 (brs, 1H); 4.40-4.25 (brs, 1H); 3.25-2.90 (m, 4H); 1.95-1.75 (m, 2H) ppm.

PREPARATION 2

Preparation of 1-tosyl-3-(R)-(−)-hydroxypyrrolidine

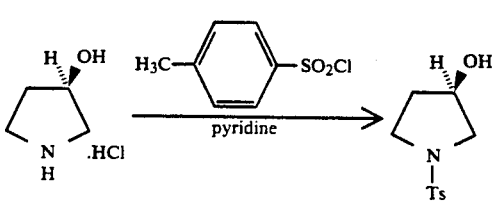

Para-toluenesulphonyl chloride (1.54 g) was added, in portions, to a solution of 3-(R)-(−)-3-hydroxypyrrolidine hydrochloride (1 g—see Preparation 1) in anhydrous pyridine (10 ml) at 0° C. The mixture was allowed to warm to room temperature and stirred for 16 hours. The solution was concentrated in vacuo and the residue was partitioned between dichloromethane (20 ml) and water (10 ml). The layers were separated and the aqueous layer was extracted with dichloromethane (2×15 ml). The combined dichloromethane extracts were washed with 2M hydrochloric acid (2×15 ml) and 10% aqueous sodium hydroxide (2×15 ml) then dried (MgSO₄) and concentrated in vacuo to give a solid which was recrystallised from ethanol to give the title compound as a colourless powder, yield 0.5 g, m.p. 108°-112° C., $[\alpha]_D^{25} -6.7°$ (c 1.0, CH₂Cl₂).

Analysis %: Found: C,54.69; H,6.23; N,5.78. Calculated for C₁₁H₁₅NO₃S: C,54.77; H,6.27; N,5.80.

¹H-N.M.R. (CDCl₃) δ=7.80-7.70 (d, 2H); 7.40-7.30 (d, 2H); 4.45-4.35 (m, 1H); 3.50-3.35 (m, 3H); 3.30-3.25 (m, 1H); 2.45 (s, 3H); 2.05-1.80 (m, 2H); 1.75-1.70 (m, 1H) ppm.

PREPARATION 3

Preparation of 1-tosyl-3-(S)-(−)-tosyloxypyrrolidine

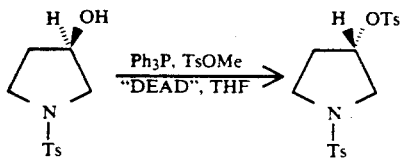

Methyl para-toluenesulphonate (54 g) was added in portions to a solution of 1-tosyl-3-(R)-(−)-hydroxypyrrolidine (49 g—see Preparation 2) and triphenylphosphine (76 g) in anhydrous tetrahydrofuran (700 ml) at 0° C. The mixture was cooled to −20° C. and diethyl azodicarboxylate (58 g—"DEAD") was added, dropwise, over 30 minutes. During this time, the temperature of the mixture was not allowed to rise above −10° C. When the addition was complete the mixture was allowed to warm to room temperature and stirred for 16 hours. The mixture was concentrated in vacuo to give a solid which was purified by column chromatography on silica eluting with hexane containing dichloromethane (50%). The product-containing fractions were combined and concentrated in vacuo to give an oil which was crystallised from 1-propanol to give the title compound as a colourless solid, yield 56 g, m.p. 110° C., $[\alpha]_D^{25} -5.2°$ (c 1.0, CH₂Cl₂).

Analysis %: Found: C,54.62; H,5.46; N,3.14. Calculated for C₁₈H₂₁NO₅S₂: C,54.66; H,5.35; N,3.54.

¹H-N.M.R. (CDCl₃) δ=7.75-7.65 (m, 4H); 7.40-7.30 (m, 4H); 5.00-4.90 (m, 1H); 3.55-3.35 (m, 3H); 3.30-3.20 (m, 1H); 2.50 (s, 3H); 2.45 (s, 3H); 2.10-1.90 (m, 2H) ppm.

PREPARATION 4

Preparation of 1-tosyl-3-(R)-(+)-tosyloxypyrrolidine

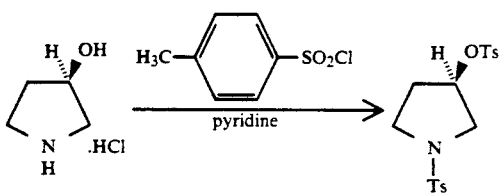

Para-toluenesulphonyl chloride (61.5 g) was added, in portions, to a solution of 3-(R)-(−)-3-hydroxypyrrolidine hydrochloride (19 g—see Preparation 1) in anhydrous pyridine (200 ml) at 0° C. The mixture was allowed to warm to room temperature and stirred for 16 hours. The solution was concentrated in vacuo and the resulting solid partitioned between dichloromethane (300 ml) and water (200 ml). The layers were separated and the aqueous layer extracted with dichloromethane (3×100 ml). The combined dichloromethane extracts were washed with 2M hydrochloric acid (2×100 ml) and 10% aqueous sodium hydroxide (2×100 ml) then dried (MgSO₄) and concentrated in vacuo to give an oil. Trituration with ether gave a solid which was recrystallised from 1-propanol to give the title compound as a colourless solid, yield 33.5 g, m.p. 111°-112° C. $[\alpha]_D^{25} +5.3°$ (c 1.0, CH₂Cl₂).

Analysis %: Found: C,54.29; H,5.39; N,3.59. Calculated for C₁₈H₂₁NO₅S₂: C,54.68; H,5.35; N,3.54.

¹H-N.M.R. (CDCl₃) δ=7.75-7.65 (m, 4H); 7.40-7.30 (m, 4H); 5.00-4.90 (m, 1H); 3.55-3.35 (m, 3H); 3.30-3.20 (m, 1H); 2.50 (s, 3H); 2.45 (s, 3H); 2.10-1.90 (m, 2H) ppm.

PREPARATION 5

Preparation of 3-(R)-1'-(R,S)-3-(1-cyano-1-phenylmethyl)-N-tosylpyrrolidine

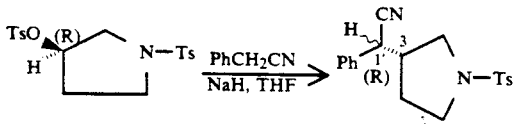

Sodium hydride (2.7 g of an 80% dispersion in mineral oil) was added, in portions, to a solution of benzyl cyanide (11.1 g) in anhydrous tetrahydrofuran (200 ml) and the mixture heated under reflux for 20 minutes then allowed to cool to room temperature. (R)-N-tosyl-3-tosyloxypyrrolidine (25 g—see Preparation 4) was added and the mixture was stirred for 16 hours at room temperature. Water (20 ml) was added and the mixture concentrated in vacuo. The residual oil was partitioned between dichloromethane (150 ml) and water (150 ml), the layers were separated and the aqueous layer was further extracted with dichloromethane (3×100 ml). The combined dichloromethane extracts were dried (MgSo₄) and concentrated in vacuo to give an oil which was purified by column chromatography on silica eluting with hexane containing diethyl ether (20%). The product-containing fractions were combined and concentrated in vacuo to give the title compounds as colourless crystals, yield, 1.5 g, m.p. 111.5° C.

¹H-N.M.R. (CDCl₃) δ=7.75-7.65 (d, 2H); 7.45-7.20 (m, 7H); 3.70-3.65 (d, 1H); 3.55-3.45 (m, 1H); 3.30-3.20 (m, 2H); 3.05-2.95 (m, 1H); 2.65-2.55 (m, 1H); 2.45 (s, 3H); 2.20-2.10 (m, 1H); 2.00-1.85 (m, 1H) ppm.

PREPARATION 6

Preparation of 3-(S)-1'-(R,S)-3-(1-cyano-1-phenylmethyl)-N-tosylpyrrolidine

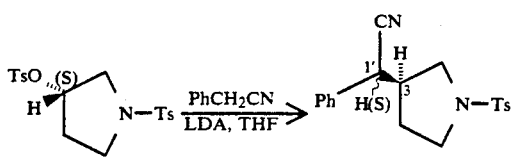

Benzyl cyanide (12.3 ml) was added, dropwise, to a solution of lithium diisopropylamide (66 ml of a 1.5M solution in hexane) in anhydrous tetrahydrofuran (50 ml) at −74° C. When the addition was complete, a solution of (S)-N-tosyl-3-tosyloxypyrrolidine (26 g—see Preparation 3) in anhydrous tetrahydrofuran (150 ml) was added dropwise. The mixture was allowed to warm to room temperature and stirred for 16 hours. The solvent was removed in vacuo and the residue partitioned between diethyl ether (100 ml) and water (100 ml). The layers were separated and the aqueous layer further extracted with diethyl ether (3×50 ml). The combined ethereal extracts were dried (MgSO₄) and concentrated in vacuo to give a yellow oil which was triturated with diisopropyl ether (4×100 ml) to give the title compounds as an oil, yield, 21.2 g.

$^1$H-N.M.R. (CDCl₃) δ=7.75–7.65 (m) 7.50–7.25 (m); 3.70–3.60 (m); 3.55–3.20 (m); 3.05–2.95 (m); 2.75–2.50 (m); 2.50 (s); 2.20–2.10 (m); 1.95–1.80 (m) ppm.

PREPARATION 7

Preparation of 3-(R)-1'-(R or S)-3-(1,3-dicyano-1-phenylprop-1-yl)-N-tosylpyrrolidine (Diastereomer A) and 3-(R)-1'-(S or R)-3-(1,3-dicyano-1-phenylprop-1-yl)-N-tosylpyrrolidine (Diastereomer B)

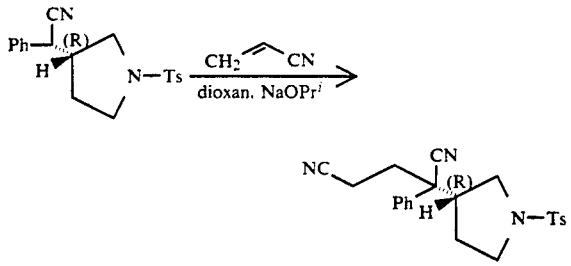

Sodium hydride (20 mg of an 80% dispersion in mineral oil) was added to 2-propanol (5 ml) and the mixture stirred at room temperature for 5 minutes. A portion (1 ml) of the resulting solution was added to a solution of 3-(R)-1'-(R,S)-3-(1-cyano-1-phenylmethyl)-N-tosylpyrrolidine (1.25 g—see Preparation 5) and acrylonitrile (0.24 g) in anhydrous dioxan (5 ml). The mixture was stirred at room temperature under a nitrogen atmosphere for 16 hours. Water (2 ml) was added and the dioxan evaporated in vacuo. The residue was diluted with water (20 ml) and extracted with dichloromethane (3×30 ml). The combined dichloromethane extracts were dried (MgSO₄) and concentrated in vacuo to give a gum which was purified by column chromatography on silica eluting with diisopropyl ether containing diethyl ether (15%). The fractions containing each separated diastereomer were combined and concentrated in vacuo to give the title compounds as gums, yield, diastereomer A 0.4 g [α]$_D^{25}$+25.6 (c 0.5, CH₂Cl₂), diastereomer B 0.45 g, [α]$_D^{25}$−52.6° (c 0.5, CH₂Cl₂).

Diastereomer A (higher Rf)

$^1$H-N.M.R. (CDCl₃) δ=7.80–7.75 (d, 2H); 7.50–7.20 (m, 7H); 3.85–3.75 (m, 1H); 3.35–3.15 (m, 3H); 2.75–2.60 (m, 1H); 2.55–2.30 (m, 3H); 2.50 (s, 3H); 2.10–1.95 (m, 1H); 1.65–1.50 (m, 2H) ppm.

Diastereomer B (lower Rf)

$^1$H-N.M.R. (CDCl₃) δ 7.70–7.60 (d, 2H); 7.55–7.40 (m, 3H); 7.40–7.30 (m, 4H); 3.45–3.35 (m, 2H); 3.10–3.05 (m, 1H); 2.85–2.75 (m, 1H); 2.70–2.60 (m, 1H); 2.45 (s, 3H); 2.45–2.30 (m, 2H); 2.40–2.00 (m, 2H); 2.05–1.85 (m, 2H) ppm.

PREPARATION 8

Preparation of 3-(S)-1'-(R or S)-3-(1,3-dicyano-1-phenylprop-1-yl)-N-tosylpyrrolidine (Diastereomer C) and 3-(S)-1'-(S or R)-3-(1,3-dicyano-1-phenylprop-1-yl)-N-tosylpyrrolidine (Diastereomer D)

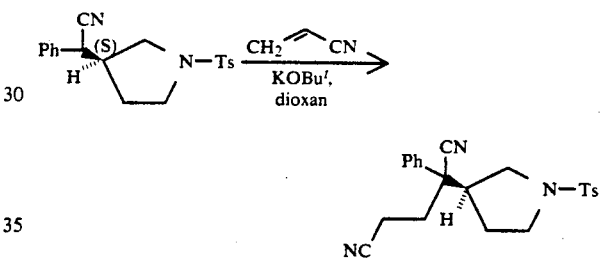

Potassium tert-butoxide (1 g) was added to a solution of acrylonitrile (3.1 g) and 3-(S)-1'-(R,S)-3-(1-cyano-1-phenylmethyl)-N-tosylpyrrolidine (21 g—see Preparation 6) in anhydrous dioxan (80 ml). The mixture was stirred at room temperature under a nitrogen atmosphere for 16 hours. Water (5 ml) was added and the dioxan was evaporated in vacuo. The residue was diluted with water (500 ml) and extracted with dichloromethane (3×200 ml). The combined dichloromethane extracts were dried (MgSO₄) and concentrated in vacuo to give an oil which was chromatographed on silica eluting with toluene containing diethyl ether (10%). The fractions containing each separated diastereomer were combined and concentrated in vacuo to give the title compounds as gums, yield, diastereomer C 9.55 g, [α]$_D^{25}$−24.4° (c 0.5 CH₂Cl₂), yield diastereomer D 5.50 g, [α]$_D^{25}$+47.8° (c 0.5 CH₂Cl₂).

Diastereomer C (higher Rf)

$^1$H-N.M.R. (CDCl₃) δ=7.80–7.75 (d, 2H); 7.60–7.20 (m, 7H); 3.85–3.75 (m, 1H); 3.35–3.15 (m, 3H); 2.70–2.60 (m, 1H); 2.50 (s, 3H); 2.50–2.30 (m, 3H); 2.10–1.95 (m, 1H); 1.65–1.50 (m, 2H) ppm.

Diastereomer D (lower Rf)

$^1$H-N.M.R. (CDCl₃) δ=7.70–7.60 (m, 2H); 7.50–7.15 (m, 7H); 3.50–3.35 (m, 2H); 3.15–3.05 (m, 1H); 2.85–2.75 (m, 1H); 2.75–2.60 (m, 1H); 2.50–2.30 (m, 2H); 2.45 (s, 3H); 2.30–2.20 (m, 2H); 2.10–1.85 (m, 2H) ppm.

PREPARATION 9

Preparation of 3-(S or R)-3'-(R)-3-phenyl-3-(pyrrolidin-3-yl)glutarimide hydrobromide

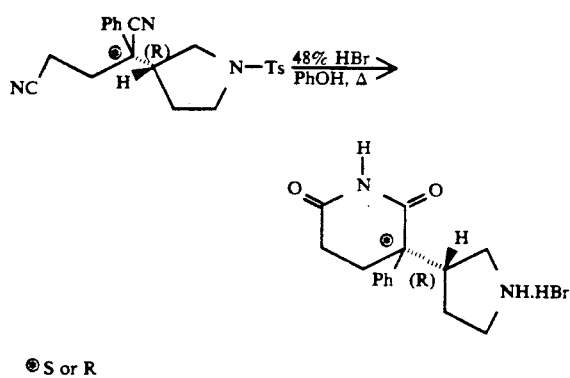

⊛ S or R

A solution of 3-(R)-1'-(S or R)-3-(1,3-dicyano-1-phenylprop-1-yl)-N-tosylpyrrolidine (0.96 g—see Preparation 7, diastereomer B) and phenol (1 g) in 48% aqueous hydrobromic acid (20 ml) was heated under reflux for 30 minutes. On cooling to room temperature, water (50 ml) was added and the mixture was extracted with ethyl acetate (3×30 ml). The aqueous mixture was concentrated in vacuo to give the title compound, yield 1.1 g, m.p. softened at 135° C., $[\alpha]_D^{25} + 96°$ (c 0.5, H$_2$O).

$^1$H-N.M.R. (d$^6$DMSO) δ=8.80–8.50 (brs); 7.50–7.30 (m, 5H); 3.25–3.00 (m, 3H); 3.00–2.80 (m, 2H); 2.60–2.40 (m, 2H); 2.40–2.25 (m, 1H); 2.10–1.95 (m, 1H); 1.90–1.75 (m, 1H); 1.75–1.60 (m, 1H) ppm.

PREPARATION 10

Preparation of 3-(R or S)-3'-(R)-3-phenyl-3-(pyrrolidin-3-yl)glutarimide hydrobromide

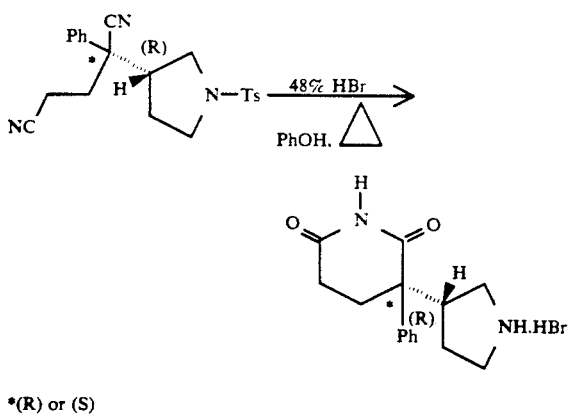

*(R) or (S)

A solution of 3-(R)-1'-(R or S)-3-(1,3-dicyano-1-phenylprop-1-yl)-N-tosylpyrrolidine (0.97 g—see Preparation 7, Diastereomer A) and phenol (1 g) in 48% aqueous hydrobromic acid was heated under reflux for 30 minutes. On cooling to room temperature water (50 ml) was added and the mixture extracted with ethyl acetate (3×30 ml). The aqueous mixture was concentrated in vacuo to give the title compound, yield 1.4 g, m.p. softened at 135° C., $[\alpha]_D^{25} - 106°$ (c 0.5, H$_2$O).

$^1$H-N.M.R. (D$_2$O) δ=7.50–7.35 (m, 5H); 3.60–3.50 (m, 1H); 3.35–3.30 (m, 1H); 3.20–3.10 (m, 1H); 3.05–2.95 (m, 2H); 2.70–2.55 (m, 2H); 2.40–2.30 (m, 2H); 2.05–1.90 (m, 2H) ppm.

PREPARATION 11

Preparation of 3-(R or S)-3'-(S)-3-phenyl-3-(pyrrolidin-3-yl)glutarimide hydrobromide

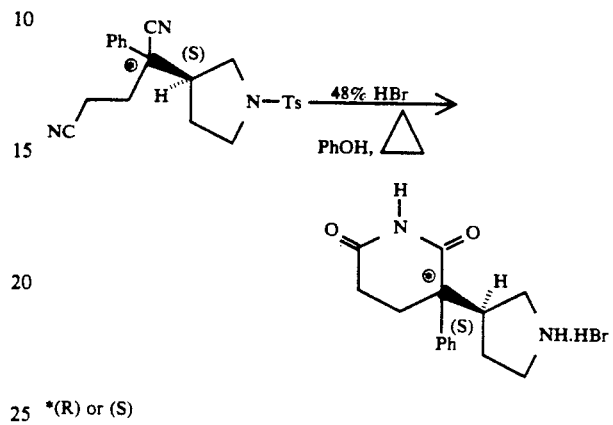

*(R) or (S)

A solution of 3-(S)-1'-(R or S)-3-(1,3-dicyano-1-phenylprop-1-yl)-N-tosylpyrrolidine (9.5 g—see Preparation 8, diastereomer C) and phenol (9.5 g) in 48% aqueous hydrobromic acid (200 ml) was heated under reflux for 30 minutes. On cooling to room temperature, water (50 ml) was added and the mixture was extracted with ethyl acetate (3×50 ml). The aqueous mixture was concentrated in vacuo to give the title compound, yield 5.8 g, $[\alpha]_D^{25} + 78.4°$ (c 0.5, H$_2$O).

$^1$H-N.M.R. (d$^6$DMSO) δ=8.70–8.50 (brs); 7.50–7.30 (m, 5H); 3.65–3.45 (brm, 2H); 3.30–3.20 (brm, 1H); 3.15–2.95 (brm, 2H); 2.85–2.65 (m, 2H); 2.60–2.45 (m, 1H); 2.35–2.20 (m, 1H); 2.15–2.00 (m, 1H); 1.80–1.70 (m, 2H) ppm.

PREPARATION 12

Preparation of 3-(S or R)-3'-(S)-3-phenyl-3-(pyrrolidin-3-yl)glutarimide hydrobromide

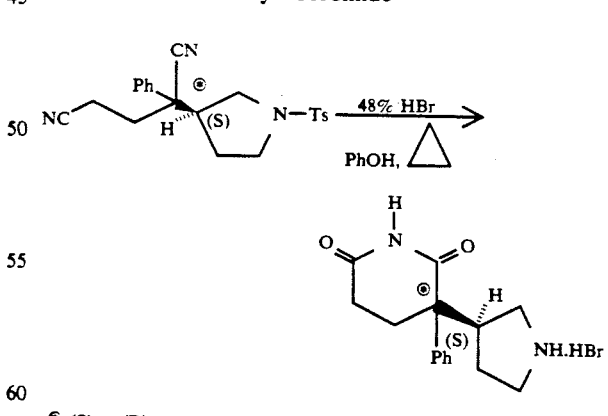

⊛ (S) or (R)

A solution of 3-(S)-1'-(S or R)-3-(1,3-dicyano-1-phenylprop-1-yl)-N-tosylpyrrolidine (5.5 g—see Preparation 8, diastereomer D) and phenol (5.5 g) in 48% aqueous hydrobromic acid (110 ml) was heated uder reflux for 30 minutes. On cooling to room temperature, water (50 ml) was added and the mixture was extracted with ethyl acetate (3×50 ml). The aqueous mixture was concentrated in vacuo to give the title compound, yield, 5.0 g, $[\alpha]_D^{25} -58.2°$ (c 0.5, H$_2$O).

$^1$H-N.M.R. (d$^6$DMSO) δ=8.95–8.65 (brs); 7.55–7.30 (m, 5H); 5.40–5.10 (brs); 3.30–3.00 (m, 3H); 2.95–2.80 (m, 2H); 2.55–2.40 (m, 2H); 2.40–2.25 (m, 1H); 2.10–1.90 (m, 1H); 1.90–1.75 (m, 1H); 1.75–1.60 (m, 1H) ppm.

PREPARATION 13

Preparation of 3-(R,S)-1'-(R,S)-3-(1-cyano-1-phenylmethyl)-N-benzyl-pyrrolidine

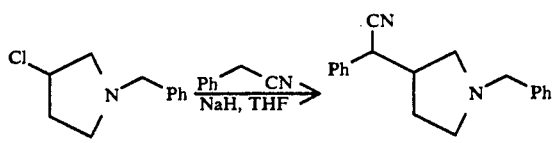

Sodium hydride (11.5 g of an 80% dispersion in mineral oil) was added, in portions, to a solution of benzyl cyanide (48 g) in anhydrous tetrahydrofuran (350 ml). The mixture was heated under reflux for 15 minutes then allowed to cool to room temperature. A solution of 3-chloro-N-benzylpyrrolidine (50 g—see J. Pharm. Sci., 56, 192, (1967)) in anhydrous tetrahydrofuran (50 ml) was added and the mixture heated under reflux for 4 hours. On cooling to room temperature, water (100 ml) and diethyl ether (200 ml) were added, the layers separated and the aqueous layer was extracted with diethyl ether (100 ml). The combined ethereal extracts were washed with water (100 ml) then dried (MgSO$_4$) and concentrated in vacuo to give an oil which was purified by column chromatography on silica eluting with dichloromethane containing diethyl ether (10%). The product-containing fractions were combined and concentrated in vacuo to give the title compound as a gum, yield 23.7 g.

Analysis %: Found: C,80.04; H,7.14; N,10.38. Calculated for C$_{19}$H$_{20}$N$_2$.⅛ CH$_2$Cl$_2$: C,80.04; H,7.11; N,9.76.

$^1$H-N.M.R. (CDCl$_3$) δ=7.45–7.20 (m, 10H); 3.85–3.75 (m, 1H); 3.70–3.55 (m, 2H); 2.90–2.60 (m, 4H); 2.60–2.50 (m, ½H); 2.35–2.30 (m, ½H); 2.25–2.10 (m, ½H); 1.95–1.85 (m, 1H); 1.70–1.55 (m, ½H) ppm.

PREPARATION 14

Preparation of 3-(R,S)-1'-(R,S)-3-(1,3-dicyano-1-phenylprop-1-yl)-N-benzylpyrrolidine

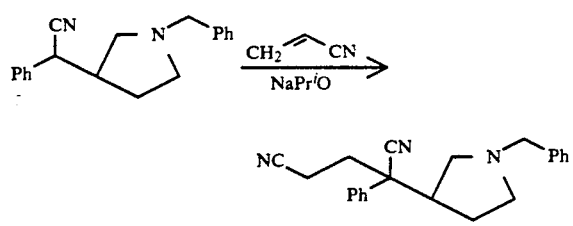

Sodium hydride (20 mg of an 80% dispersion in mineral oil) was added to 2-propanol (5 ml) and the mixture stirred at room temperature for 5 minutes. A portion (1 ml) of the resulting solution was added to a solution of 3-(R,S)-1'-(R,S)-3-(1-cyano-1-phenylmethyl)-N-benzyl-pyrrolidine (20 g—see Preparation 13) and acrylonitrile (5 g) in anhydrous dioxan (50 ml). The resulting solution was stirred at room temperature for 16 hours then concentrated in vacuo. Water (50 ml) was added and the mixture extracted with diethyl ether (2×100 ml). The combined ethereal extracts were dried (MgSO$_4$) and concentrated in vacuo to give a gum which was purified by column chromatography on silica eluting with hexane containing diethyl ether (50% up to 100%). The product-containing fractions were combined and concentrated in vacuo to give the title compound as a gum, yield 8.1 g.

$^1$H-N.M.R. (CDCl$_3$) δ=7.50–7.20 (m); 3.70 (s); 3.70–3.45 (Abq); 3.15–3.10 (m); 2.95–2.75 (m); 2.60–1.90 (m); 1.75–1.45 (m).

PREPARATION 15

Preparation of 3-(R,S)-3'-(R,S)-3-phenyl-3-(pyrrolidin-3-yl)glutarimide formate

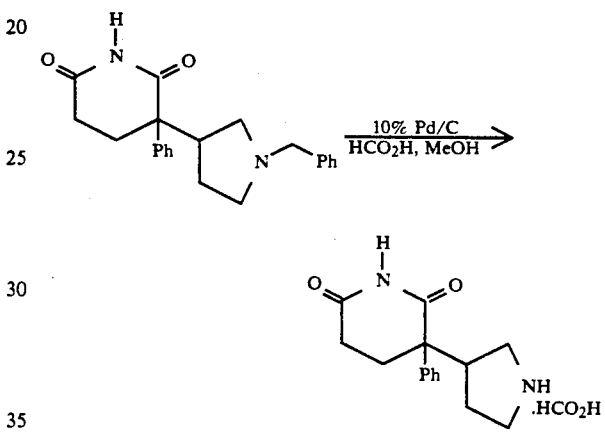

10% Palladium-on-carbon (1.5 g) was added, in portions, to an ice-cold solution of 3-(R,S)-3'-(R,S)-3-phenyl-3-(N-benzyl-pyrrolidin-3-yl)glutarimide (2.8 g—see Example 7). The mixture was allowed to warm to room temperature and stirred for 24 hours. The catalyst was filtered off and the filtrate concentrated in vacuo to give the title compound as a foam, yield 1.8 g.

Analysis %: C,64.66; H,6.79; N,9.67. Calculated for C$_{15}$H$_{18}$N$_2$O$_2$.HCO$_2$H: C,63.15; H,6.62; N,9.20.

$^1$H-N.M.R. (CDCl$_3$) δ=8.55 (s), 7.45–7.00 (m), 3.75–3.55 (m), 3.55–3.30 (m), 3.30–2.70 (m), 2.70–2.10 (m), 2.10–1.60 (m) ppm.

PREPARATION 16

Preparation of 5-(2-hydroxyethyl)-2,3-dihydrobenzofuran

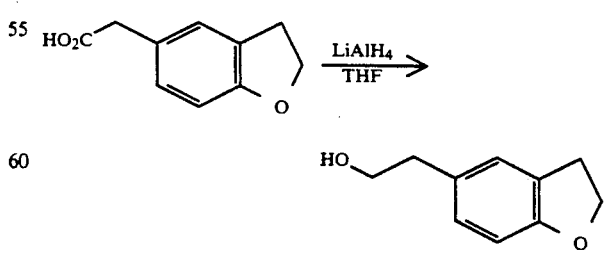

A solution of (2,3-dihydrobenzofuran-5-yl)acetic acid (4.9 g—see EP-A-132130) in anhydrous tetrahydrofuran (50 ml) was added dropwise over 10 minutes to a stirred suspension of lithium aluminium hydride (1.57 g)

in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide (1.5 ml) and, finally, water (4.5 ml). The mixture was filtered and the inorganic salts washed with ethyl acetate (2×50 ml). The filtrate and washings were combined and concentrated in vacuo to give the title compound as an oil, yield 3.3 g.

$^1$H-N.M.R. (CDCl$_3$) $\delta$=7.10 (s, 1H); 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (brs, 1H) ppm.

PREPARATION 17

Preparation of 5-(2-bromoethyl)-2,3-dihydrobenzofuran

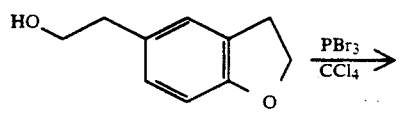

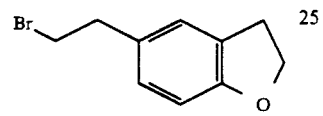

Phosphorus tribromide (0.37 g) was added to a solution of 5-(2-hydroxyethyl)-2,3-dihydrobenzofuran (0.612 g—see Preparation 16) in carbon tetrachloride (3 ml) and the mixture was heated under reflux for 3 hours. On cooling to room temperature, the mixture was partitioned between 10% aqueous sodium carbonate (20 ml) and dichloromethane (20 ml). The layers were separated and the aqueous layer was extracted with dichloromethane (2×10 ml). The combined dichloromethane extracts were dried (MgSO$_4$) and concentrated in vacuo to give the title compound as an oil which crystallised on standing, yield 0.584 g, m.p. 60°–62° C.

$^1$H-N.M.R. (CDCl$_3$) $\delta$=7.10 (s, 1H); 7.00–6.95 (d, 1H); 6.80–6.70 (d, 1H); 4.65–4.55 (t, 2H); 3.60–3.50 (t, 2H); 3.25–3.15 (t, 2H); 3.15–3.10 (t, 2H) ppm.

We claim:
1. A compound of the formula:

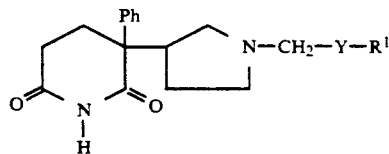

or a pharmaceutically acceptable salt thereof, wherein
Y is, —CH$_2$—, —(CH$_2$)$_2$—, —CH$_2$O— or —CH$_2$S—; and
R$^1$ is a group of the formula:

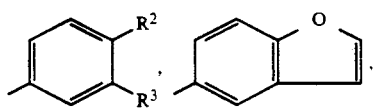

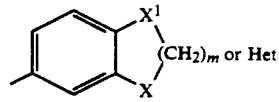

where
R$^2$ and R$^3$ are each independently H, C$_1$-C$_4$ alkyl, C$_1$-C$_4$ alkoxy, —(CH$_2$)$_n$OH, halo, trifluoromethyl, cyano, —(CH$_2$)$_n$NR$^4$R$^5$, —CO(C$_1$-C$_4$ alkyl), —OCO(C$_1$-C$_4$ alkyl), —CH(OH) (C$_1$-C$_4$ alkyl), —C(OH) (C$_1$-C$_4$ alkyl)$_2$, —SO$_2$NH$_2$, —(CH$_2$)$_n$CONR$^4$R$^5$ or —(CH$_2$)$_n$COO(C$_1$-C$_4$ alkyl);
R$^4$ and R$^5$ are each independently H or C$_1$-C$_4$ alkyl;
n is 0, 1 or 2;
X and X$^1$ are each independently O or CH$_2$;
m is 1, 2 or 3; and
"Het" is pyridyl, pyrazinyl or thienyl.
2. A compound as claimed in claim 1 wherein m is 1.
3. A compound as claimed in claim 2 wherein R$^1$ is a group of the formula:

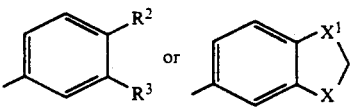

where R$^2$ and R$^3$ are each independently selected from H, halo and hydroxy, and X and X$^1$ are each independently O or CH$_2$.
4. A compound as claimed in claim 3 wherein Y is —CH$_2$— or —(CH$_2$)$_2$—.
5. A compound as claimed in claim 4, wherein Y is —CH$_2$—.
6. A compound as claimed in claim 3 wherein R$^1$ is:

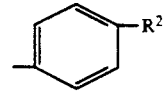

wherein R$^2$ is selected from hydrogen, fluorine, chlorine and hydroxy, and Y is —CH$_2$— or —(CH$_2$)$_2$—.
7. A compound as claimed in claim 3 wherein R$^1$ is:

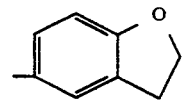

8. A compound as claimed in claim 7 wherein Y is —CH$_2$—.
9. A pharmaceutical composition comprising a compound of the formula (I) as claimed in claim 1, or a pharmaceutically acceptable salt thereof, and a pharmaceutically acceptable diluent or carrier.
10. A method for treating irritable bowel disease in a patient in need of such treatment, which comprises administering to said patient an effective amount of a compound of the formula (I) or pharmaceutically acceptable salt thereof as claimed in claim 1.

* * * * *